United States Patent [19]
Van Boeckel et al.

[11] Patent Number: 5,872,110
[45] Date of Patent: Feb. 16, 1999

[54] HEPARIN-LIKE DERIVATIVES

[75] Inventors: Constant Adriaan Anton Van Boeckel, Gmercuriusstraat; Pieter Westerduin, Vlierbes, both of Netherlands

[73] Assignee: Akzo Nobel N.V. and Sanofi, Arnhem, Netherlands

[21] Appl. No.: 876,107

[22] Filed: Apr. 30, 1997

[30] Foreign Application Priority Data

May 8, 1996 [EP] European Pat. Off. ............. 96201267

[51] Int. Cl.$^6$ ...................... A61K 31/725; C08B 37/10
[52] U.S. Cl. ................ 514/56; 514/822; 536/21
[58] Field of Search .............. 514/56, 822; 536/21, 536/120, 122, 123

[56] References Cited

U.S. PATENT DOCUMENTS

| | | | |
|---|---|---|---|
| 5,514,659 | 5/1996 | Petitou et al. | 514/25 |
| 5,543,403 | 8/1996 | Petitou et al. | 514/54 |
| 5,707,973 | 1/1998 | Baron et al. | 514/56 |

FOREIGN PATENT DOCUMENTS

| | | |
|---|---|---|
| 0300099 | 1/1989 | European Pat. Off. . |
| 0301618 | 2/1989 | European Pat. Off. . |
| 0454220 | 10/1991 | European Pat. Off. . |
| 0529715 | 3/1993 | European Pat. Off. . |

*Primary Examiner*—Howard C. Lee
*Attorney, Agent, or Firm*—William M. Blackstone; Gregory R. Muir

[57] ABSTRACT

The invention relates to carbohydrate derivatives having the formula I,

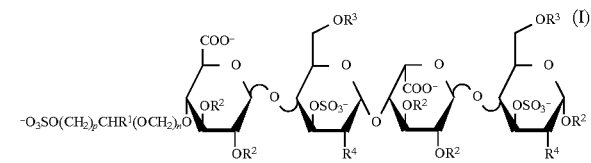

wherein $R^1$ is H or $CH_2OSO_3^-$, $R^2$ and $R^3$ are independently H, (1–6C)alkyl or $SO_3^-$; $R^4$ is $OSO_3^-$ or $NHSO_3^-$; n is 0 or 1; p is 1 or 2; or a pharmaceutically acceptable salt thereof The compounds of the invention have antithrombotic activity and may be used for inhibiting smooth muscle cell proliferation.

8 Claims, 4 Drawing Sheets

HEPARIN-LIKE DERIVATIVES

BACKGROUND OF THE INVENTION

The invention relates to a carbohydrate derivative having antithrombotic activity, a pharmaceutical composition containing the same, as well as the use of said carbohydrate derivative for the manufacture of a medicament.

Carbohydrate derivatives having antithrombotic activity are known, for example the sulfated glycosaminoglycan derivatives disclosed in EP 84,999. Other sulfated glycosaminoglycan-related carbohydrate derivatives are disclosed in EP 529,715, having improved pharmacological properties. These carbohydrate derivatives are devoid of the characteristic functional groups of glycosaminoglycans, being free hydroxyl groups, N-sulfate and N-acetyl groups.

SUMMARY OF THE INVENTION

It has now been found that the carbohydrate derivatives of this invention having the formula I,

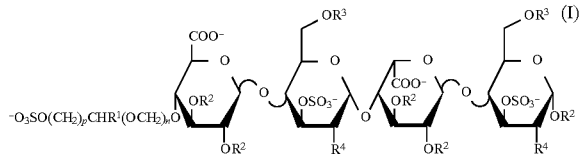

wherein $R^1$ is H or $CH_2OSO_3^-$; $R^2$ and $R^3$ are independently H, (1–6C)alkyl or $SO_3^-$; $R^4$ is $OSO_3^-$ or $NHSO_3^-$; n is 0 or 1; p is 1 or 2; or a pharmaceutically acceptable salt thereof, have an anti-Xa activity which is substantially higher than that of saccharides not having the glycerol-like or glycol-like group at the 4-position of the non-reducing end.

Factor Xa plays an important role in the blood coagulation cascade. It catalyzes the formation of thrombin which regulates the last step in the coagulation cascade. The prime function of thrombin is the cleavage of fibrinogen to generate fibrin monomers, which form an insoluble gel, a fibrin clot, by cross-linking.

The compounds of the present invention are useful for treating and preventing thrombin-mediated and thrombin-associated diseases. This includes a number of thrombotic and prothrombotic states in which the coagulation cascade is activated which include, but are not limited to, deep vein thrombosis, pulmonary embolism, thrombophlebitis, arterial occlusion from thrombosis or embolism, arterial reocclusion during or after angioplasty or thrombolysis, restenosis following arterial injury or invasive cardiological procedures, postoperative venous thrombosis or embolism, acute or chronic atherosclerosis, stroke, myocardial infarction, cancer and metastasis, and neurodegenerative diseases. The carbohydrate derivatives of the invention may also be used as inhibitors of smooth muscle cell proliferation and for the treatment of angiogenesis, cancer and retrovirus infections, like HIV. Further, the compounds of the invention may be used as anticoagulants and anticoagulant coatings in extracorporeal blood circuits, as necessary in dialysis and surgery. The compounds of the invention may also be used as in vitro or ex vivo anticoagulants.

DETAILED DESCRIPTION OF THE PREFERRED EMBODIMENT

Preferred carbohydrate derivatives according to the invention have the formula I, wherein $R^2$ is (1–6C)alkyl, $R^3$ is $SO_3^-$, $R^4$ is $OSO_3^-$, and $R^1$, n and p are as previously defined; or a pharmaceutically acceptable salt thereof.

More preferred carbohydrate derivatives have formula I wherein $R^1$ is methyl. Particularly preferred carbohydrate derivatives have formula I, wherein n is 1 and p is 1. Most preferred are carbohydrate derivatives of formula I, wherein $R^1$ is $CH_2OSO_3^-$.

The term (1–6C)alkyl means a branched or unbranched alkyl group having 1 to 6 carbon atoms, such as methyl, ethyl, isopropyl, t-butyl, isopentyl, hexyl, and the like. Preferred alkyl groups are (1–4C)alkyl groups, such as methyl, ethyl, (iso)propyl, n-butyl and t-butyl. The most preferred alkyl group is methyl.

The counter-ions which compensate the charged moieties are pharmaceutically acceptable counter-ions, like hydrogen, or more preferably alkali or earth-alkali metal ions, like sodium, calcium, or magnesium.

The carbohydrate derivatives according to this invention may be prepared by coupling of a protected glycerol-like or glycol-like moiety to the 4-hydroxy group of the non-reducing end of a further protected tetrasaccharide, which may be produced according to the method described by Westerduin P., Bioorg. and Med. Chem., 2, 1267–1280, 1994. Hereafter, the protecting groups are removed, followed by sulfation of the compound, resulting in a carbohydrate derivative of formula I.

For the treatment of venous thrombosis or for the inhibition of smooth muscle cell proliferation the compounds of the invention may be administered enterally or parenterally, and for humans preferably in a daily dosage of 0.001–10 mg per kg body weight. Mixed with pharmaceutically suitable auxiliaries, e.g. as described in the standard reference, Gennaro et al., Remington's Pharmaceutical Sciences, (18th ed., Mack Publishing Company, 1990, see especially Part 8: Pharmaceutical Preparations and Their Manufacture), the compounds, when orally, buccally or sublingually active, may be compressed into solid dosage units, such as pills, tablets, or be processed into capsules or suppositories. By means of pharmaceutically suitable liquids the compounds can also be applied as an injection preparation in the form of a solution, suspension, emulsion, or as a spray, e.g. a nasal spray. For making dosage units, e.g. tablets, the use of conventional additives such as fillers, colorants, polymeric binders and the like is contemplated. In general any pharmaceutically acceptable additive which does not interfere with the function of the active compounds can be used. Suitable carriers with which the compositions can be administered include lactose, starch, cellulose derivatives and the like, or mixtures thereof, used in suitable amounts.

BRIEF DESCRIPTION OF THE DRAWINGS

FIG. 2 Depicts a flow sheet to make heparin-like derivatives by using a glycerol derivative as an alkylating agent.

The invention is further illustrated by the following examples.

Figure 1A:
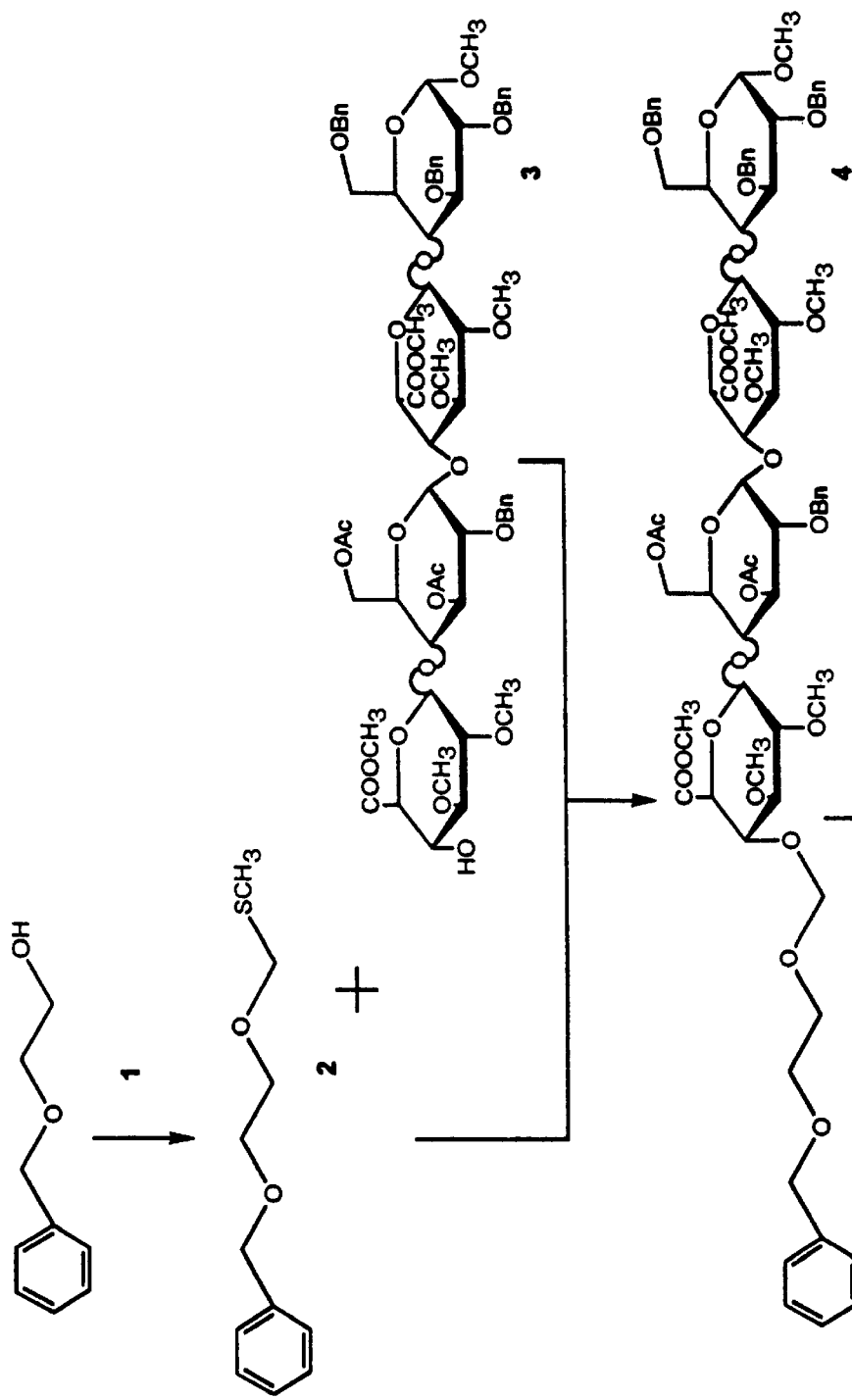
FIG. 1 Depicts a flow sheet to make heparin-like derivatives by using a 2-benzyloxyethanol/chloromethyl methyl sulfide alkylating agent.
Figure 1B:
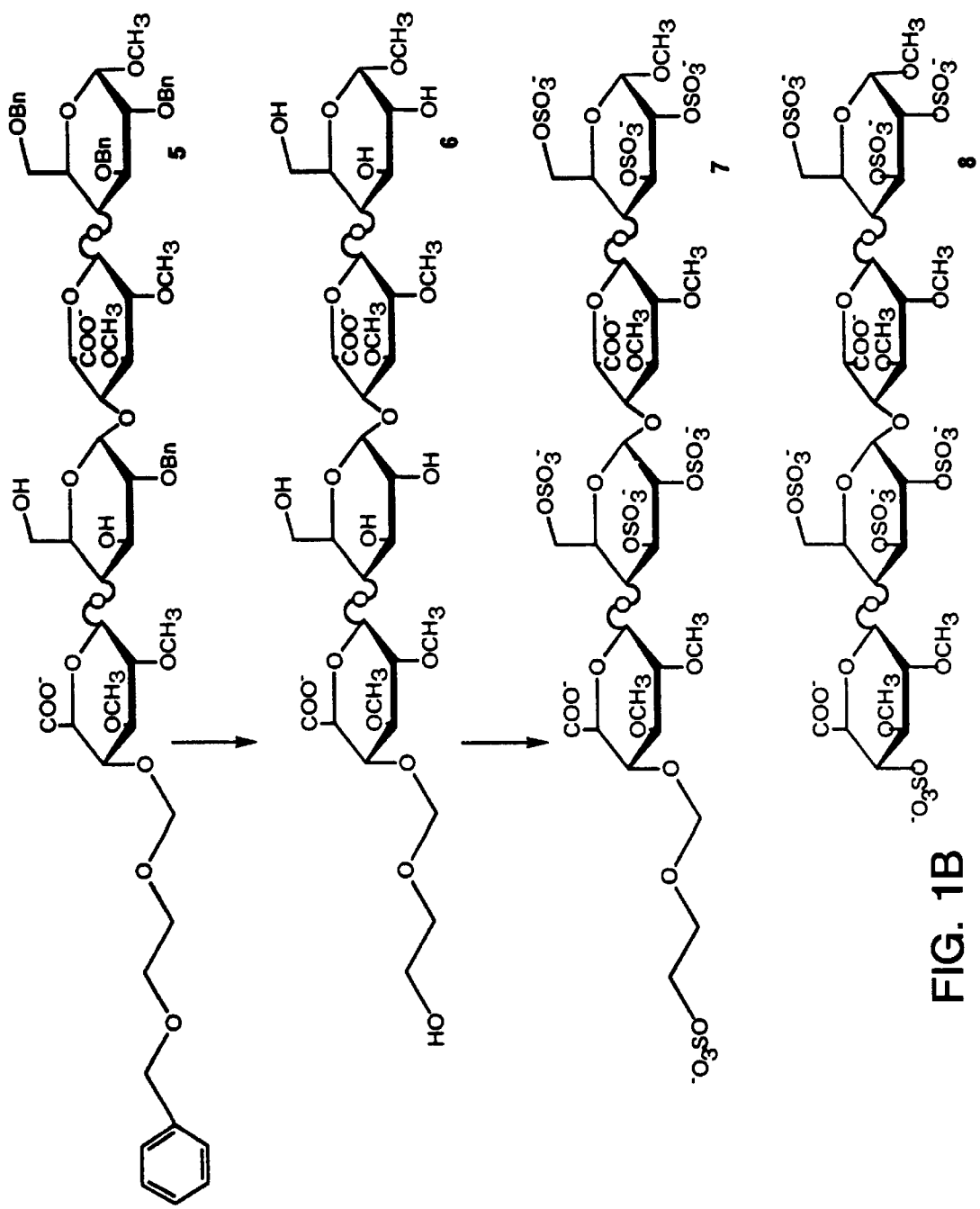
Figure 1C:
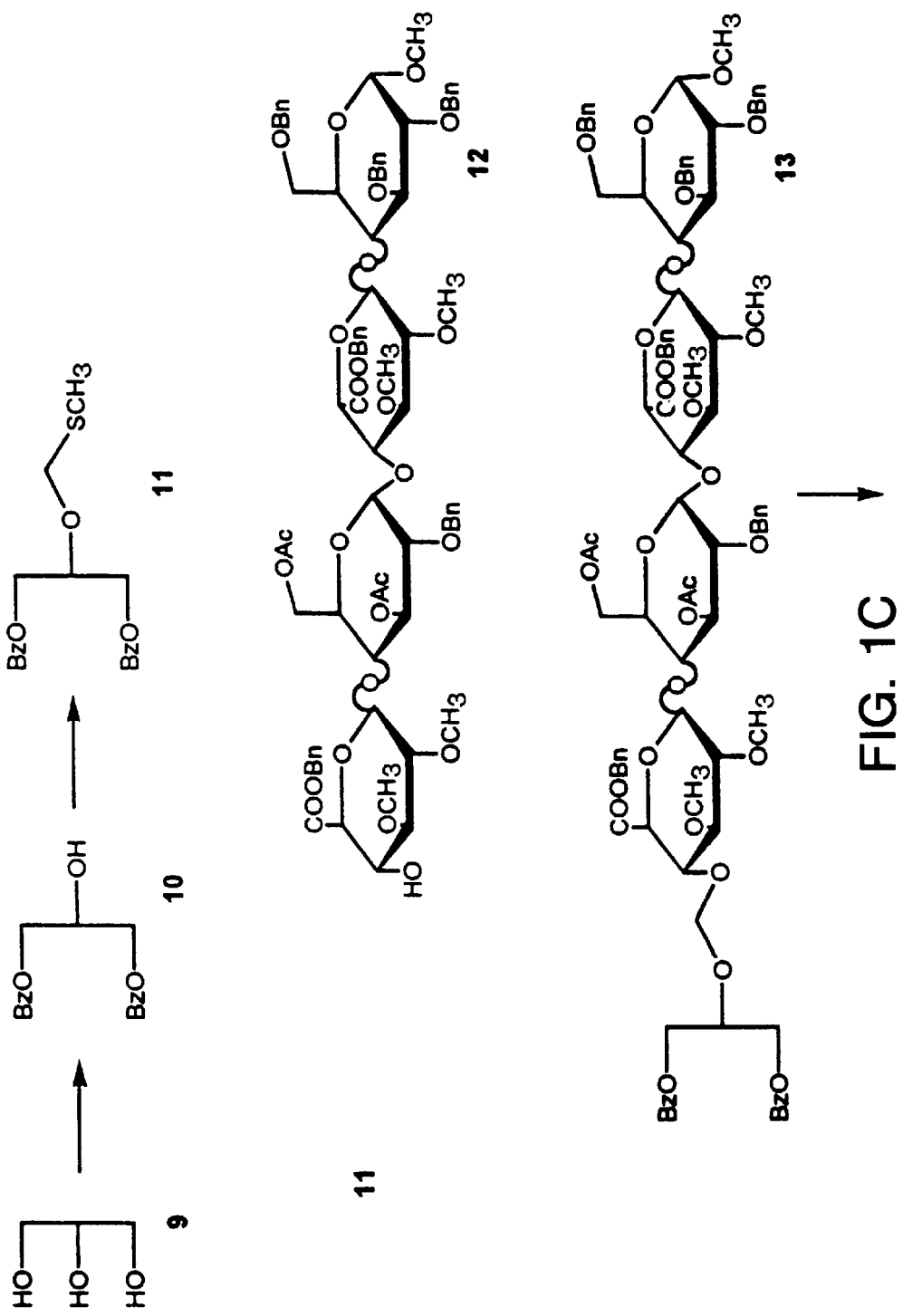
Figure 1D:
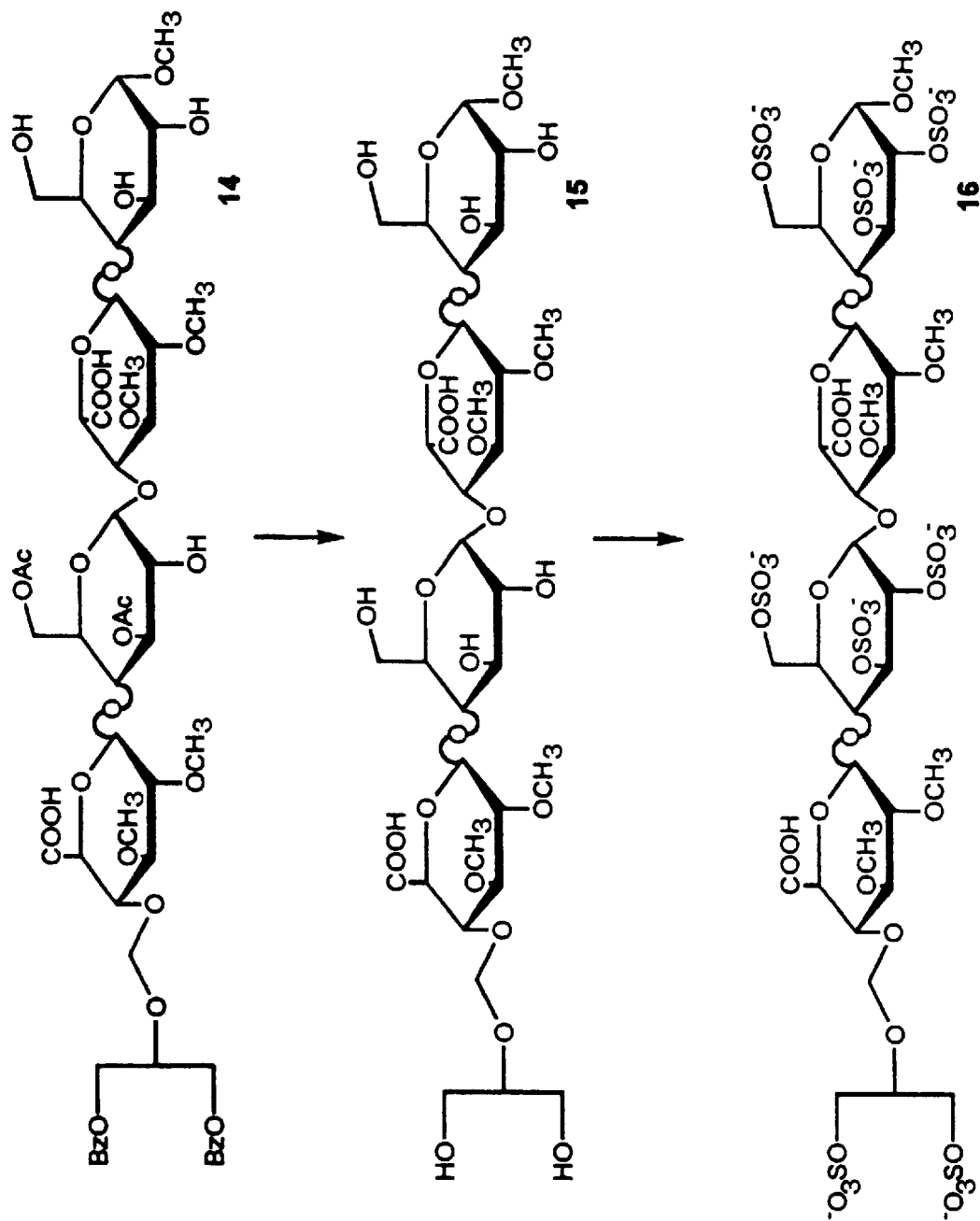

(In the examples reference is made to flow sheets 1 and 2 (i.e. FIGS. 1 and 2). The intermediates and end-products are indicated by reference to the corresponding number on the flow sheets)

EXAMPLE 1

Preparation of Compound 7 and 8

Preparation of 2

To a cooled (0° C.) solution of 2-benzyloxyethanol 1 (2.84 ml) and chloromethyl methyl sulfide (1.59 ml) in ethylene glycol dimethyl ether (25 ml) was added sodium hydride, 60% dispersion in mineral oil (1.2 g) under nitrogen atmosphere and the mixture was stirred for 20 h at room temperature. Methanol was added to the reaction mixture and stirring was continued for 15 min. The mixture was diluted with ethyl acetate (100 ml), subsequently washed with aqueous sodium hydrogen carbonate and water and the organic layer was dried over magnesium sulfate and concentrated in vacuo. The crude product was purified by silica gel column chromatography to give 2.5 g of 2.

Preparation of 3

The synthesis of 3 has been described in Bioorganic and Medicinal Chemistry, vol 2, no. 11, pp 1267–1280, 1994 (P. Westerduin et al.).

Preparation of 4

A mixture of 3 (125 mg), 2 (64 mg) and powdered molecular sieves (4 Å) in dichloromethane (1.5 ml) was stirred under a nitrogen atmosphere for 15 min. The solution was cooled (5° C.) and a freshly prepared solution containing N-iodosuccinimide (68 mg) and trifluoromethanesulphonic acid (2.7 µl) in 1.5 ml of 1,2-dichloroethane—dioxane (1/1, v/v) was introduced. After 10 min the red reaction mixture was filtered, diluted with dichloromethane, washed successively with aqueous sodium thiosulfate and aqueous sodium hydrogen carbonate. The organic layer was dried over magnesium sulfate and concentrated in vacuo. The residue was purified by size exclusion chromatography on a Sephadex LH-20 suspended in dichloromethane-methanol (2/1, v/v) to furnish 108 mg of 4.

Preparation of 5

To a cooled (−5° C.) solution of 4 (105 mg) in tetrahydrofuran (7.3 ml) a 30% aqueous solution of hydrogen peroxide (3.8 ml) was added and after 10 min stirring a lithium hydroxide solution (1.25M, 1.7 ml) was added. The mixture was stirred for 2 h at −5° C., after which the temperature was raised to 0° C. After 20 h stirring the temperature was raised to 20° C. and stirring was continued for 24 h. The reaction mixture was cooled (0° C.), subsequently methanol (7.0 ml) and aqueous sodium hydroxide (4M, 2.0 ml) were added. After stirring for 1 h the temperature was raised again to 20° C. and stirring was continued for another 20 h. The mixture was cooled (0° C.), acidified to pH 3 with hydrochloric acid (2N) and extracted with dichloromethane. The organic layer was washed with aqueous sodium sulfite (5%), dried over magnesium sulfate and concentrated in vacuo. The crude product was purified by silica gel column chromatography to give 80 mg of 5.

Preparation of 6

To a solution of 6 (80 mg) in a mixture of water (7 ml) and 2-methyl-2-propanol (7 ml) 80 mg of palladium on charcoal (10%) was added. The reaction mixture was placed under a hydrogen atmosphere for 16 h. The catalyst was removed by filtration and rinsed with 2-methyl-2-propanol/water mixtures. The filtrate and washings were concentrated in vacuo and lyophilized to give 38 mg of 6.

Preparation of 7 and 8

A solution of 6 (38 mg) in water (0.8 ml) was eluted with water over a Dowex 50WX8H$^+$ column and the pooled fractions were evaporated to dryness. After evaporation with N,N-dimethylformamide the residue was dissolved in N,N-dimethylformamide (2.5 ml), placed under an nitrogen atmosphere and triethylamine sulfurtrioxide complex (287 mg) was added. The mixture was stirred overnight at 50° C., cooled to 0° C. and an aqueous solution of sodium hydrogen carbonate (533 mg) was added. The mixture was stirred for 1 h at 20° C., concentrated to a small volume and desalted on a Sephadex G-25 column suspended in water:acetonitrile 9:1 (v/v). The crude product was eluted on a Dowex 50WX8Na$^+$ column and purified by anion exchange column chromatography (HPLC, Mono-Q 5/5, sodium chloride gradient) to give 12 mg of 7.{$[\alpha]^{20}_D$=+31.1 (c=1; water)} and 18 mg of 8 {$[\alpha]^{20}_D$=34.8 (c=0.93; water)}.

EXAMPLE 2

Preparation of Compound 16

Preparation of 10

A solution of benzoyl chloride (26,3 ml) in dry dioxane (26 ml) was added dropwise during 1 h to a cooled (−20° C.) mixture of glycerol (10 g) and pyridine (109 ml). The resulting mixture was stirred for 16 h at 0° C., after which water was added. After 15 min stirring the mixture was concentrated to one fifth of its volume, diluted with dichloromethane and washed with water, aqueous sodium hydrogen carbonate and water. The organic layer was dried over magnesium sulphate and concentrated in vacuo. The resulting oil was purified by silica gel column chromatography to give 21 g of 10.

Preparation of 11

Methyl sulfide (1.45 ml) was added to a solution of 10 (600 mg) in acetonitrile:dichloromethane (1:1, v/v; 8 ml). The reaction mixture was cooled to 0° C. and a mixture of dry benzoylperoxide (3.63 g) in acetonitrile:dichloromethane (1:1, v/v; 10 ml) was added dropwise. After stirring for 16 h at 20° C. the mixture was diluted with dichloromethane and washed with aqueous sodium hydrogen carbonate and water. The organic layer was dried over magnesium sulfate and concentrated in vacuo. After purification by silica gel column chromatography 400 mg of 11 was isolated.

Preparation of 12

Compound 12 was prepared analogously to the procedures described by P. Westerduin et al. Bioorganic and Medicinal Chemistry 1994, vol 2, no. 11, pp. 1267–1280. During the reaction steps to afford 12 the uronic acids were protected by benzyl groups instead of methyl groups.

Preparation of 13

Compound 13 was prepared in a manner similar as described for compound 4 by coupling compound 11 to compound 12.

Preparation of 14

A suspension of sodium hydrogencarbonate (142 mg) in water (2 ml) and Pd/C (400 mg) were added to a solution of 13 (480 mg) in 2-methyl-2-propanol (60 ml). The mixture was placed in an atmosphere of hydrogen for 16 h. The catalyst was removed by filtration and washed with 2-methyl-2-propanol/water mixtures. The combined filtrate and washings were concentrated in vacuo to give 315 mg of 14, which was used without further purification.

Preparation of 15

Compound 14 (315 mg) was dissolved in 0.35N aqueous sodium hydroxide (10 ml). The reaction mixture was stirred overnight after which the pH was adjusted to 8.5 with 1N hydrochloride acid. The mixture was desalted on a Sephadex G-25 column suspended in a mixture of water:acetonitril:triethylamine 90:10:0.1 (v/v/v). The appropriate fractions were pooled and concentrated in vacuo. The product was again subjected to hydrogenolysis in a similar manner as described for compound 14. After work up and concentration of the filtrate and washings, the mixture was desalted on Sephadex G-25 column suspended in a mixture of water- :acetonitril:triethylamine 90:10:0.1 (v/v/v). The appropriate fractions were pooled, concentrated in vacuo, eluted on a Dowex 50WX8Na$^+$ column with water and finally lyophilised to give 165 mg of 15.

Preparation of 16

A solution of 15 (165 mg) was evaporated with N,N-dimethylformamide and dissolved in N,N-dimethylformrnamide (11.0 ml). Triethylamine sulfurtrioxide complex (1.31 g) was added to the reaction mixture. After stirring for 16 h at 50° C., the mixture was cooled (0° C.) aqueous sodium hydrogen carbonate (2.43 g) was added and stirring was continued for 1 h at 20° C. after which the solution was concentrated in vacuo. The residue was desalted on a Sephadex G-25 column suspended in water-acetonitrile 9:1 (v/v) and the appropriate fractions were pooled and concentrated in vacuo. After elution on a Dowex 50WX8Na$^+$ column the product was purified on a Q-Sepharose High Load column using a sodium chloride gradient, to give 160 mg of 16. $\{[\alpha]^{20}_D=+24.0\ (c=0.77, H_2O)\}$.

We claim:

1. A carbohydrate derivative having the formula I

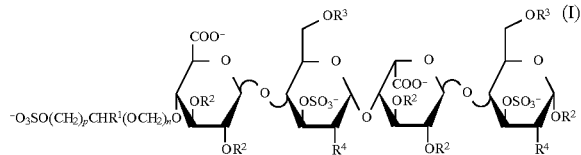

wherein $R^1$ is H or $CH_2OSO_3^-$;

$R^2$ and $R^3$ are independently H, (1–6C)alkyl or $SO_3^-$;

$R^4$ is $OSO_3^-$ or $NHSO_3^-$;

n is 0 or 1;

p is 1 or 2;

or a pharmaceutically acceptable salt thereof.

2. The carbohydrate derivative of claim 1 wherein is $R^2$ is (1–6C)alkyl, $R^3$ is $SO_3^-$, $R^4$ is $OSO_3^-$.

3. The carbohydrate derivative of claim 2, wherein $R^2$ is methyl.

4. The carbohydrate derivative of claim 1, wherein n is 1 and p is 1.

5. The carbohydrate derivative of claim 1, wherein $R^1$ is $CH_2OSO_3^-$.

6. A pharmaceutical composition comprising the carbohydrate derivative of claim 1 and pharmaceutically suitable auxiliaries.

7. A method of treating or preventing a thrombotic or prothrombotic condition comprising administering to a patient in need thereof the carbohydrate derivative of claim 1 having anti-thrombotic activity.

8. A method of making a pharmaceutical composition comprising admixing or combining the carbohydrate derivative of claim 1 with one or more pharmaceutically acceptable auxiliaries.

* * * * *

UNITED STATES PATENT AND TRADEMARK OFFICE
CERTIFICATE OF CORRECTION

PATENT NO. : 5,872,110
DATED : February 16, 1999
INVENTOR(S) : C.A.A. van Boeckel It is certified that error appears in the above-identified patent and that said Letters Patent is hereby corrected as shown below:

On the title page, item [75], deleting Gmercuriusstraat and Vlierbes and replacing each with --Oss--.

Signed and Sealed this

Ninth Day of May, 2000

Attest:

Q. TODD DICKINSON

*Attesting Officer*    *Director of Patents and Trademarks*